United States Patent
Shepherd, Jr.

(10) Patent No.: US 7,226,583 B2
(45) Date of Patent: Jun. 5, 2007

(54) COMPOSITION CONTAINING LEUKOCYTE EXTRACT FOR THE WHITENING OR LIGHTENING OF SKIN

(75) Inventor: Walter B. Shepherd, Jr., Warwick, NY (US)

(73) Assignee: Hair Systems, Inc., Englishtown, NJ (US)

( * ) Notice: Subject to any disclaimer, the term of this patent is extended or adjusted under 35 U.S.C. 154(b) by 676 days.

(21) Appl. No.: 10/638,221

(22) Filed: Aug. 8, 2003

(65) Prior Publication Data

US 2004/0028712 A1 Feb. 12, 2004

Related U.S. Application Data

(60) Provisional application No. 60/403,205, filed on Aug. 12, 2002.

(51) Int. Cl.
*A61Q 19/02* (2006.01)
*A61K 36/00* (2006.01)

(52) U.S. Cl. .................. 424/62; 424/400; 424/401; 424/735; 424/736; 424/739; 424/757; 424/758

(58) Field of Classification Search ................ 424/62, 424/400, 401, 735, 736, 739, 757, 758
See application file for complete search history.

(56) References Cited

U.S. PATENT DOCUMENTS

| | | | |
|---|---|---|---|
| 4,818,768 A | 4/1989 | Nazzaro-Porro | |
| 5,279,834 A | 1/1994 | Meybeck | |
| 5,747,006 A | 5/1998 | Dornoff | |
| 5,882,658 A | 3/1999 | Simon | |
| 5,980,904 A | 11/1999 | Leverett | |
| 6,077,503 A | 6/2000 | Dornoff | |
| 6,123,959 A | 9/2000 | Jones | |

FOREIGN PATENT DOCUMENTS

RU R2 191 000 C2 * 8/2000

* cited by examiner

*Primary Examiner*—Shelley A. Dodson
(74) *Attorney, Agent, or Firm*—Blank Rome LLP

(57) ABSTRACT

Cosmetic compositions intended for topical application to the skin for lightening and/or brightening the skin are provided. The subject compositions are characterized by the presence of leukocyte extract in combination with one or more secondary skin whitening or brightening agents. A preferred group of such agents includes bearberry, arbutin, rutin, ascorbyl glucoside, ascorbyl magnesium phosphate, hydroquinone, kojic acid or combinations thereof. Another group of preferred agents includes extracts of mulberry, lemon, orange, licorice, cucumber, cinnamon, cherry (fermentate), rosemary and/or derivatives thereof. It has been found that the combination of leukocyte extract with such agents possesses enhanced efficacy over similar preparations that do not contain leukocyte extract.

22 Claims, No Drawings

US 7,226,583 B2

COMPOSITION CONTAINING LEUKOCYTE EXTRACT FOR THE WHITENING OR LIGHTENING OF SKIN

RELATED APPLICATIONS

This application is a continuation of U.S. Provisional Application No. 60/403,205, filed Aug. 12, 2002.

FIELD OF THE INVENTION

This invention relates to skin whitening and lightening compositions including leukocyte extract in combination with an additional lightening or whitening agent in a composition for topical application to the skin.

BACKGROUND OF THE INVENTION

The use of skin lightening cosmetics varies significantly among cultures. In Western countries, for example, skin lighteners are applied for the prevention or treatment of melasma, freckles (lentigo aesticva), age spots (lentigo senilis), or to "even out" skin tone in general. In Asian and African nations, the primary use of skin lighteners is to make the skin whiter, lighter and/or brighter.

The pigments contributing to the color of the skin are carotenoids, hemoglobin and melanin. Melanin, however, is produced in melanocytes which are the pigment-forming cells in the basal layers of the epidermis and, as such, will largely determine the color of the skin. Numerous cosmetic compositions have recently been developed to reduce the amount of melanin in the skin. The majority of these products achieve reduction in melanin by inhibiting tyrosinase, which is apparently the only essential enzyme in the biosynthesis of melanin.

There are a number available tyrosinase inhibitors used in cosmetic compositions. One of the first tyrosinase inhibitors used in skin lightening was hydroquinone, used either alone or in combination with other functional materials such as kojic acid, as described in U.S. Pat. No. 5,279,834 (Meybek). These materials apparently give only temporary effect, and hyperpigmentation returns if use of the described composition is discontinued.

More recently, bearberry, arbutin and rutin (usually derived from botanical sources) have been found to be effective tyrosinase inhibitors, as disclosed in U.S. Pat. Nos. 5,980,904 (Leverett), 6,123,959 (Jones), and 5,882,658 (Simon), respectively. These preparations seem to have a cumulative effect and, with continued use, hyperpigmentation may be controlled with less frequent application of the compositions.

Functional tyrosinase inhibitors such as those mentioned above have also been used in combination with other agents. U.S. Pat. No. 5,747,006 (Dornoff) discusses a combination of acerola cherry fermentate with bearberry extract, arbutin, kojic acid and various free radical scavengers and/or botanical extracts. Similarly, U.S. Pat. Nos. 6,077,503 (Dornoff) and 4,818,768 (Nazzaro-Porro) disclose the use of mercaptodexran and mercapto-derivatives of dicarboxylic acid, respectively, in combination with free radical scavengers, arbutin, kojic acid and/or various botanical extracts.

Compositions such as the above seem to be effective, to varying degrees, in whitening or lightening the skin, but room for improvement still exists.

SUMMARY OF THE INVENTION

In accordance with the present invention, there are provided cosmetic compositions for the lightening and/or whitening of skin by inhibiting the formation of melanin. The subject compositions possess enhanced efficacy resulting from the combination of leukocyte extract an additional lightening and/or brightening agent, such as at least one of bearberry extract, arbutin, rutin or ascorbic acid or its derivatives. "Enhanced efficacy," as used herein, means that the cosmetic compositions of the present invention exhibit an increased rate of visible lightening and/or whitening of the skin, and cumulative lightening. Preferably, with continued use, the frequency of application required to achieve the desired level of lightening and/or of whitening of the skin may decrease.

The present invention also includes a method for the lightening and/or whitening of the skin that comprises applying to the skin an effective amount of a composition containing leukocyte extract in combination with an additional lightening and/or brightening agent for a period of time sufficient to visibly lighten and/or whiten the skin.

The cosmetic compositions of the present invention may be prepared in the form of a liquid, lotion, cream, paste, gel, serum, tablet or granular powder that may be formed into a suitable fluid preparation, and may contain other component materials recognized in the cosmetic industry as being suitable for incorporation into such preparations. Examples of such component materials include emollients, emulsifiers, thickeners and/or gelling agents, moisturizers, solvents, preservatives, colorants and fragrances.

DETAILED DESCRIPTION OF THE INVENTION

In accordance with the present invention, a skin lightening and/or whitening composition is provided that comprises leukocyte extract in combination with one or more secondary lightening and/or whitening agents. It has been found that cosmetic skin lightening compositions containing leukocyte extract in combination with one or more secondary lightening and/or whitening agent or agents achieve a higher degree of efficacy than similar compositions lacking leukocyte extract.

The enhanced performance realized from the combination of leukocyte extract and a secondary lightening and/or whitening agent is not restricted to specific examples of such agents. For example, enhanced performance has been observed in cosmetic compositions comprising leukocyte extract in combination with bearberry extract, arbutin, rutin, ascorbic acid, ascorbyl glucoside, ascorbyle magnesium phosphate, mercaptodextran, hydroquinone or kojic acid. Preferred among this group of secondary agents are bearberry extract, arbutin, rutin, ascorbic acid or its derivatives.

The compositions provided in accordance with the present invention further includes compositions wherein leukocyte extract is combined with secondary functional lightening and/or whitening agents selected from the group of agents derived from natural and/or botanical sources. This group of functional agents includes, but is not limited to, extracts of mulberry, lemon, orange, licorice, cucumber, cinnamon, cherry (fermentate), rosemary and/or derivatives thereof. The actual amount of these natural or botanically derived functional agents comprising the cosmetic composition of this invention will vary significantly due to the wide variation in the activity of extracts of this nature. The desired level of the secondary functional agent and the ratio of the secondary functional agent to leukocyte extract is determined experimentally on the basis of preferred performance criteria.

Typically, the cosmetic compositions of the present invention comprise leukocyte extract in a concentration of from about 0.5% to about 99.0% by weight, preferably from about 0.5% to about 20.0% by weight, and a secondary functional lightening and/or whitening agent as described above in a concentration of from about 0.5% to about 99.0% by weight, preferably from about 0.5% to about 20.0% by weight. The weight ratio of the leukocyte extract to secondary functional agent typically varies from about 400:1 to about 1:400 and preferably from about 10:1 to about 1:10 by weight. More preferably, the subject compositions contain approximately equal quantities of leukocyte extract and the secondary functional lightening and/or whitening agent.

The compositions of the present invention preferably contain antioxidants and free radical scavengers to aid in the protection of the skin. Preferred examples of such agents include, without intended limitation, vitamin E, vitamin A, tea tree oil (Melaleuca Altemifolia), butylated hydroxyanisole (BHA), butylated hydroxytoluene (BHT), cysteine, erythrobic acid, ferulic acid or derivatives thereof. Preferably, these agents comprise from about 0.05% to about 15.0% by weight, more preferably from about 0.05% to about 5.0% by weight, of the cosmetic compositions of the present invention.

The subject compositions also preferably contain one or more art-recognized chelating agents to enhance the stability of the compositions. Various chelating agents may also enhance the efficacy of the subject compositions in that they are also recognized as being effective tyrosinase inhibitors, presumably due to their ability to chelate copper at a pH between 3.0 and 7.0 (tyrosinase being a multifunctional, glycoslated, copper-containing oxidase). Chelating agents effective in cosmetic compositions of the present invention include, without intended limitation, ethylenediaminetetraacetic acid (EDTA), citric acid, gluconic acid, β-cyclodextran, hydroxyethylenediaminetetraacetic acid (HEDTA), their derivatives and salts thereof.

The cosmetic compositions comprising the present invention are topically applied to the skin in an amount and for a time sufficient to visibly lighten and/or whiten the skin. Consequently, the cosmetic compositions of this invention are prepared in the form of a cosmetically and/or pharmaceutically acceptable matrix or vehicle which is suitable for such application. Such compositional forms include a liquid, lotion, cream, paste, gel, serum and the like. For convenience, the compositions of the invention may be formulated in dry form, such as tablets or powders, that will form a suitable fluid preparation upon mixing with water, e.g. a solution, suspension or emulsion. The physical form of the product, to a degree, will determine the specific method of application but in all cases the cosmetic compositions will be topically applied to the skin, for example, by spraying, wiping, rubbing, swabbing, and the like. The matrix or pharmaceutical vehicle will comprise from about 1.0% to about 99.0% by weight, preferably from about 25.0% to about 99.0% by weight, of the subject cosmetic compositions.

The cosmetic compositions of the present invention will additionally contain various conventional and commercially available cosmetic ingredients typically utilized to prepare such compositions. will generally be used to prepare the matrix or vehicle of the present invention. In general, these ingredients may include materials intended to function as emulsifiers, surfactants, emollients, e.g. fatty esters, waxes, and/or essential oils, moisturizers, humectants, stabilizers, viscosity modifiers, gelling agents, colorants, lubricants, diluents, absorbents, astringents, fragrances, propellants, conditioners, sunscreen agents, ultraviolet light absorbers and/or preservatives. Those skilled in the art of cosmetic compounding will recognize that the selection of these ingredients will be in part governed by the type of preparation being prepared. For example, a propellant would only be contemplated in the preparation of an aerosol solution, suspension or emulsion. Generally, the cosmetic ingredients comprising the present invention include, without intended limitation, any ingredient listed in the *International Cosmetic Ingredient Dictionary and Handbook*, (published by The Cosmetic, Toiletry and Fragrance Association, Washington, D.C., 20036-4702).

The efficacy of the cosmetic composition comprising the present invention was evaluated by both panel and in vitro testing. It was found that the efficacy of the compositions was maximized when they were prepared to be at a pH of between about 3.0 and 7.0, preferably at a pH between 4.0 and 6.5, irrespective of the specific secondary functional lightening and/or whitening agent used in combination with the leukocyte extract.

The following examples are designed to demonstrate the efficacy of the present invention, and are not in any manner intended to limit the scope thereof.

EXAMPLE 1

| INGREDIENT | % BY WEIGHT |
|---|---|
| Water-deionized | 77.75 |
| Cetyl alcohol | 2.50 |
| Isopropyl myristate | 2.50 |
| Glyceryl stearate | 1.00 |
| Glyceryl stearate (and) PEG-100 stearate | 1.50 |
| Stearic acid | 2.00 |
| Squalane | 0.50 |
| Triethanolamine | 0.75 |
| Leukocyte extract | 5.00 |
| Bearberry extract | 5.00 |
| Ascorbic acid | 0.50 |
| Phenoxyethanol | 0.40 |
| Methylparaben | 0.30 |
| Propylparaben | 0.30 | pH adjusted to 6.5 with Citric Acid

The above cosmetic composition was formulated as a viscous white cream by conventional compounding techniques. The cream, which had a mild odor, was panel tested against the same composition: (1) containing 10.0% bearberry extract alone; and (2) containing 10.0% leukocyte extract alone. The composition containing the blend of leukocyte and bearberry extracts was found to be more effective than either of the two equivalent compositions having a the same amount of either agent alone. The composition of Example 1 containing the combination of leukocyte and bearberry extracts lightened and/or whitened the skin of the test subjects in a shorter period of time, and when use was discontinued, the localized skin discoloration did not return as quickly.

EXAMPLE 2

| INGREDIENT | % BY WEIGHT |
|---|---|
| Water-deionized | 82.85 |
| Carbomer | 0.50 |
| Triethanolamine | 0.35 |
| Glycerin | 2.50 |
| Sodium hyaluronate | 0.05 |
| Sodium EDTA | 0.25 |
| Leukocyte extract | 7.50 |
| Bearberry extract | 5.00 |
| Propylene glycol | 0.20 |
| Diazolidinyl urea | 0.40 |
| Methylparaben | 0.20 |
| Propylparaben | 0.20 | pH adjusted to 6.5 with Citric Acid

The above cosmetic composition was formulated as a viscous translucent gel by conventional compounding techniques. The gel, which had a mild odor, was panel tested against the same composition, but containing 12.5% bearberry extract alone and 12.5% leukocyte extract alone, respectively. As was found in Example 1, the composition containing the blend of leukocyte extract and bearberry extract was found to be more effective than either of the two equivalent compositions having the same amount of either agent alone. Further, as found in Example 1, the composition containing the combination of leukocyte extract and bearberry extract lightened and/or whitened the skin of the test subjects in a shorter period of time, and when use was discontinued, the localized skin discoloration did not return as quickly.

EXAMPLE 3

A cream prepared in accordance with the formulation of Example 1 except containing 4.0% of each of leukocyte extract and bearberry extract was panel tested against a commercial product containing 5.0% hydroquinone as the active ingredient. In this instance, there appeared to be no significant difference in the rate at which the two products lightened and/or whitened the skin of the test subjects. However, when use was discontinued, the localized discoloration of the skin returned much quicker in the areas where the commercial hydroquinone product was used. It was further noted that the commercial hydroquinone product was irritating to skin whereas the composition of Example 3 was not.

Accordingly, it can be seen that cosmetic compositions of the present invention comprising leukocyte extract in combination with a secondary lightening and/or whitening agent exhibit enhanced lightening and/or whitening of the skin, and a slower repigmentation upon discontinuing application. Further, the cosmetic compositions of the present invention appear to be less irritating to the skin than cosmetic compositions containing hydroquinone.

What is claimed is:

1. A composition for lightening or whitening human skin, comprising an effective amount of leukocyte extract and an additional lightening or brightening agent selected from the group consisting of bearberry, arbutin, rutin, ascorbyl glucoside, ascorbyl magnesium phosphate, hydroquinone, kojic acid or combinations thereof, and a pharmaceutical vehicle suitable for topical application, wherein the composition comprises from 0.5% to 99% by weight of leukocyte extract.

2. A composition in accordance with claim 1, wherein the composition is in the form of a cream, lotion, paste, ointment, emulsion, gel, foam, liquid spray or a tablet or powder that will form a suitable fluid preparation upon mixing with water.

3. A composition in accordance with claim 1 wherein the composition comprises from 0.5% to 99% by weight of said additional lightening or brightening agent selected from the group consisting of bearberry, arbutin, rutin, ascorbyl glucoside, ascorbyl magnesium phosphate, hydroquinone, kojic acid or combinations thereof.

4. A composition in accordance with claim 1, wherein said composition has a pH between about 3.0 and 7.0.

5. A composition in accordance with claim 4, wherein said composition has a pH between about 4.0 and 6.5.

6. A composition in accordance with claim 1, further comprising an agent selected from the group consisting of antioxidants, free radical scavengers, chelating agents and combinations thereof.

7. A composition in accordance with claim 6, wherein said antioxidants and free radical scavengers are selected from the group consisting of vitamin E, vitamin A, tea tree oil, butylated hydroxyanisole, butylated hydroxytoluene, cysteine, erythrobic acid, ferulic acid or derivatives thereof and combinations thereof, and the chelating agent is selected from the group consisting of ethylenediaminetetraacetic acid, citric acid, gluconic acid, B-cyclodextran, hydroxyethylenediaminetetraacetic acid, their derivatives, their salts and mixtures thereof.

8. A composition for lightening or whitening human skin, comprising an effective amount of leukocyte extract and an additional lightening or brightening agent selected from the group consisting of extracts of mulberry, lemon, orange, licorice, cucumber, cinnamon, cherry (fermentate), rosemary and/or derivatives thereof or combinations thereof, and a pharmaceutical vehicle suitable for topical application, wherein the composition comprises from 0.5% to 99% by weight of leukocyte extract.

9. A composition in accordance with claim 8, wherein the composition is in the form of a cream, lotion, paste, ointment, emulsion, gel, foam, liquid spray or a tablet or powder that will form a suitable fluid preparation upon mixing with water.

10. A composition in accordance with claim 8, wherein the composition comprises from 0.5% to 99% by weight of said additional lightening or brightening agent selected from the group consisting of extracts of mulberry, lemon, orange, licorice, cucumber, cinnamon, cherry (fermentate), rosemary and/or derivatives thereof or combinations thereof.

11. A composition in accordance with claim 8, wherein said composition has a pH between about 3.0 and 7.0.

12. A composition in accordance with claim 11, wherein said composition has a pH between about 4.0 and 6.5.

13. A composition in accordance with claim 8, further comprising an agent selected from the group consisting of antioxidants, free radical scavengers, chelating agents and combinations thereof.

14. A composition in accordance with claim 13, wherein said antioxidants and free radical scavengers are selected from the group consisting of vitamin E, vitamin A, tea tree oil, butylated hydroxyanisole, butylated hydroxytoluene, cysteine, erythrobic acid, ferulic acid or derivatives thereof and combinations thereof, and the chelating agent is selected from the group consisting of ethylenediaminetetraacetic acid, citric acid, gluconic acid, B-cyclodextran, hydroxyethylenediaminetetraacetic acid, their derivatives, their salts and mixtures thereof.

15. A method of whitening or lightening human skin comprising applying to the skin an effective amount of a composition in accordance with claim 1.

16. A method of whitening or lightening human skin comprising applying to the skin an effective amount of a composition in accordance with claim 8.

17. A composition in accordance with claim 1, wherein the composition comprises from 0.5% to 20.0% by weight of leukocyte extract.

18. A composition in accordance with claim 1, wherein the ratio of leukocyte extract to additional lightening or brightening agent is about 400:1 to about 1:400.

19. A composition in accordance with claim 1, wherein the ratio of leukocyte extract to additional lightening or brightening agent is about 10:1 to about 1:10.

20. A composition in accordance with claim 8, wherein the composition comprises from 0.5% to 20.0% by weight of leukocyte extract.

21. A composition in accordance with claim 8, wherein the ratio of leukocyte extract to additional lightening or brightening agent is about 400:1 to about 1:400.

22. A composition in accordance with claim 8, wherein the ratio of leukocyte extract to additional lightening or brightening agent is about 10:1 to about 1:10.

* * * * *